United States Patent
Rapoport et al.

(10) Patent No.: US 9,272,105 B2
(45) Date of Patent: Mar. 1, 2016

(54) SYSTEM AND METHOD FOR DIAGNOSIS AND TREATMENT OF OBSTRUCTIVE SLEEP APNEA

(75) Inventors: David M. Rapoport, New York, NY (US); Robert G. Norman, New Windsor, NY (US); Indu A. Ayappa, New York, NY (US)

(73) Assignee: NEW YORK UNIVERSITY, New York, NY (US)

( * ) Notice: Subject to any disclaimer, the term of this patent is extended or adjusted under 35 U.S.C. 154(b) by 882 days.

(21) Appl. No.: 12/833,402

(22) Filed: Jul. 9, 2010

(65) Prior Publication Data
US 2012/0010519 A1    Jan. 12, 2012

(51) Int. Cl.
*A61B 5/08* (2006.01)
*A61M 16/00* (2006.01)
*A61B 5/087* (2006.01)

(52) U.S. Cl.
CPC ............... *A61M 16/00* (2013.01); *A61B 5/087* (2013.01); *A61M 16/0066* (2013.01); *A61M 2016/0021* (2013.01); *A61M 2016/0039* (2013.01)

(58) Field of Classification Search
CPC combination set(s) only.
See application file for complete search history.

(56) References Cited

U.S. PATENT DOCUMENTS

| | | | |
|---|---|---|---|
| 6,299,581 B1 | 10/2001 | Rapoport et al. | |
| 6,988,994 B2 | 1/2006 | Rapoport et al. | |
| 7,013,893 B2 * | 3/2006 | Wickham et al. | 128/204.23 |
| 2004/0087866 A1 | 5/2004 | Bowman et al. | |
| 2005/0268912 A1 | 12/2005 | Norman et al. | |
| 2006/0102179 A1 | 5/2006 | Rapoport et al. | |
| 2008/0053442 A1 | 3/2008 | Estes et al. | |
| 2008/0092894 A1 | 4/2008 | Nicolazzi et al. | |

FOREIGN PATENT DOCUMENTS

| CN | 101 309 716 | 11/2008 |
|---|---|---|
| JP | 2008 264181 | 11/2008 |
| WO | 2006/102707 | 10/2006 |

OTHER PUBLICATIONS

"AutoSet T, Clinician's Manual", ResMed Limited, 1999, 59 sheets.

* cited by examiner

*Primary Examiner* — Michael Kahelin
*Assistant Examiner* — Mitchell E Alter
(74) *Attorney, Agent, or Firm* — Fay Kaplun & Marcin, LLP

(57) ABSTRACT

A system for diagnosis and treatment of breathing disorders in a patient, comprises a flow generator supplying an air flow to an airway of a patient via a flow path, a venting arrangement moveable between (i) a closed position in which the flow path is substantially sealed between the flow generator and the patient's airway and (ii) an open position in which the flow path is open to an ambient atmosphere, a sensor detecting data corresponding to flow through the patient's airway, and a processing arrangement controlling operation of the venting arrangement and the flow generator, wherein, in a diagnostic mode, the processing arrangement maintains the venting arrangement in the open position and in a therapeutic mode, the processing arrangement maintains the venting arrangement in the closed position and controls the flow generator to supply to the patient's airway via the flow path a calculated therapeutic pressure.

22 Claims, 5 Drawing Sheets

AIRFLOW TO AND
FROM CPAP GENERATOR

AIRFLOW TO AND
FROM CPAP GENERATOR

AIRFLOW TO AND
FROM CPAP GENERATOR

AIRFLOW TO AND
FROM CPAP GENERATOR

AIRFLOW TO AND
FROM CPAP GENERATOR

SYSTEM AND METHOD FOR DIAGNOSIS AND TREATMENT OF OBSTRUCTIVE SLEEP APNEA

BACKGROUND

Obstructive sleep apnea syndrome (OSAS) is a well-recognized disorder which may affect as much as 1-5% of the adult population. OSAS is one of the most common causes of excessive daytime somnolence and is most frequent in obese males. It is the single most frequent reason for referral to sleep disorder clinics. OSAS is associated with all conditions in which there is an anatomic or functional narrowing of a patient's upper airway, and is characterized by an intermittent obstruction of the upper airway during sleep. The obstruction results in a spectrum of respiratory disturbances ranging from the total absence of airflow (apnea) to significant obstruction with or without reduced airflow (hypopnea and snoring), despite continued respiratory efforts. The morbidity of the syndrome arises from hypoxemia, hypercapnia, bradycardia and sleep disruption associated with the apneas and arousals from sleep.

The pathophysiology of OSAS has not been fully worked out. However, it is now well recognized that obstruction of the upper airway during sleep is in part due to the collapsible behavior of the supraglottic segment of the airway during the negative intraluminal pressure generated by inspiratory effort. Thus, during sleep, the upper airway behaves substantially as a Starling resistor. That is, the flow through the upper airway is limited to a fixed value irrespective of the driving (inspiratory) pressure. With the loss of airway tone characteristic of the onset of sleep and which may be exaggerated in OSAS, partial or complete airway collapse may occur.

Since 1981, positive airway pressure (PAP) applied by a tight fitting nasal mask worn during sleep has evolved as the most effective treatment for this disorder. The availability of this non-invasive form of therapy has resulted in extensive publicity for apnea and the appearance of large numbers of patients who previously may have avoided the medical establishment because of the fear of intubation and/or tracheostomy. Increasing the comfort of the system (e.g., comfortable masks, minimizing applied nasal pressure, etc.) to improve patient compliance with therapy has been a major goal of research.

PAP therapy has become the mainstay of treatment in Obstructive Sleep Disordered Breathing (OSDB), which includes Obstructive Sleep Apnea, Upper Airway Resistance Syndrome, Snoring, exaggerations of sleep induced rises in collapsibility of the upper airway and all conditions in which inappropriate collapsing of a segment of the upper airway causes significant obstruction to airflow. This collapse generally occurs whenever pressure in the collapsible portion of the airway becomes sub-atmospheric or, more accurately, becomes lower than a "tissue pressure" in the surrounding wall. PAP therapy is directed to maintaining pressure in the collapsible portion of the airway at or above the critical "tissue pressure" at all times. This goal has previously been achieved by raising the airway pressure in the entire respiratory system to a level higher than this critical pressure.

Despite its success, limitations to the use of PAP still exist. Most limitations take the form of discomfort from the mask and the nasal pressure required to obliterate the apneas. Determining the minimum effective pressure remains a goal of the preliminary testing of a patient in the sleep laboratory. However, it has been shown that this required pressure varies throughout the night with sleep stage and body position. Furthermore, the therapeutic pressure may both rise and fall over time in patients with changing anatomy (e.g., nasal congestion/polyps), changes in weight, changing medication or with alcohol use. Consequently, most sleep laboratories currently prescribe the setting for home use of nasal PAP based upon the single highest value of pressure needed to obliterate apneas during a night of monitoring in the sleep laboratory. Retesting may often be necessary if the patient complains of incomplete resolution of daytime sleepiness, and may reveal a change in the required pressure.

There are also limitations to the diagnosis of OSAS which requires monitoring airflow at the nose and mouth. Algorithms are available for the diagnostic criteria using a nasal cannula/pressure traducer system to detect characteristic changes in the nasal airflow system which identify airflow obstruction (i.e., flow limitation events). In particular, a diagnostic study must be performed before the nasal PAP is prescribed. This diagnosis may include a titration study in a laboratory or the use of an autotitration device. However, these procedures may only be justified after a preliminary diagnostic study has been performed.

In many OSAS treatment centers, diagnosis and initiation of the PAP therapy are frequently combined into a single night of monitoring a patient. For example, current Medicare guidelines require a two hour minimum of monitoring in a diagnostic mode to complete the diagnosis of OSAS. The diagnosis may also be performed during ambulatory and/or unattended monitoring. However, the benefit of the unattended monitoring decreases if, for example, a second night and separate equipment are needed to initiate the PAP therapy.

Although there are some "smart" PAP systems that adjust their applied pressure based on various criteria, these systems cannot decrease their pressure to "zero" pressure due to the potential for the build up of excessive levels of $CO_2$. Certain PAP systems used in scientific research allow for zero pressure. However, these systems are suitable only for diagnosis and are not capable of delivering therapeutic pressures.

SUMMARY OF THE INVENTION

The present invention is directed to a system for diagnosis and treatment of breathing disorders in a patient, the system comprising a flow generator supplying an air flow to an airway of a patient via a flow path, a venting arrangement moveable between (i) a closed position in which the flow path is substantially sealed between the flow generator and the patient's airway and (ii) an open position in which the flow path is open to an ambient atmosphere, a sensor detecting data corresponding to one of flow and pressure through the patient's airway, and a processing arrangement controlling operation of the venting arrangement and the flow generator. In a diagnostic mode, the processing arrangement maintains the venting arrangement in the open position and monitors airflow through the patient's airway using the data provided by the sensor. In a therapeutic mode, the processing arrangement maintains the venting arrangement in the closed position and controls the flow generator to supply to the patient's airway via the flow path a therapeutic pressure calculated based on the data compiled in the diagnostic mode.

BRIEF DESCRIPTION OF THE DRAWINGS

The accompanying drawings which are incorporated in and constitute part of the Specification, illustrate several embodiments of the invention and, together with the description, serve to explain examples of the present invention. In the drawings.

DETAILED DESCRIPTION

FIGS. 1-5 illustrate waveforms of flow from a PAP generator obtained during the testing of a patient in sleep studies. In these tests, the patient was wearing a PAP mask connected to an air source, for example, in the manner illustrated in U.S. Pat. No. 5,065,765. Each of these FIGS. 1-5 illustrates an epoch of 30 seconds, with the vertical lines depicting seconds during the tests. FIGS. 1-5 depict separate sweeps that were taken from 1 to 2 minutes apart with different pressures from the air source.

Figure 1:
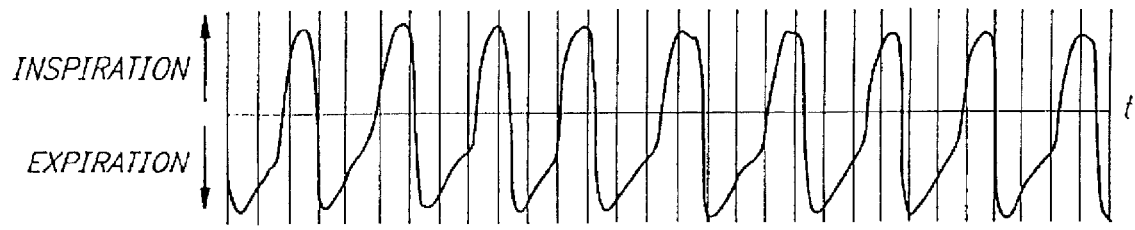
FIG. 1 shows a waveform of airflow from a sleeping patient in a 30 second epoch when subjected to a substantially constant PAP pressure of 10 cm $H_2O$.

FIG. 1 illustrates a "normal" waveform, in this instance with a Continuous Positive Airway Pressure ("CPAP") of 10 cm $H_2O$. Although this description uses a CPAP system to illustrate the system and method according to the present invention, those skilled in the art will understand that this invention is equally useful in conjunction with any PAP systems. However, any other pressure identified as corresponding to apnea free respiration may also be used. It is noted that this waveform, at least in the inspiration periods, is substantially sinusoidal. The waveforms of FIGS. 2-5 illustrate that, as the CPAP is lowered, a predictable index of increasing collapsibility of the airway occurs, prior to the occurrence of frank apnea, periodic breathing or arousal.

Figure 2:
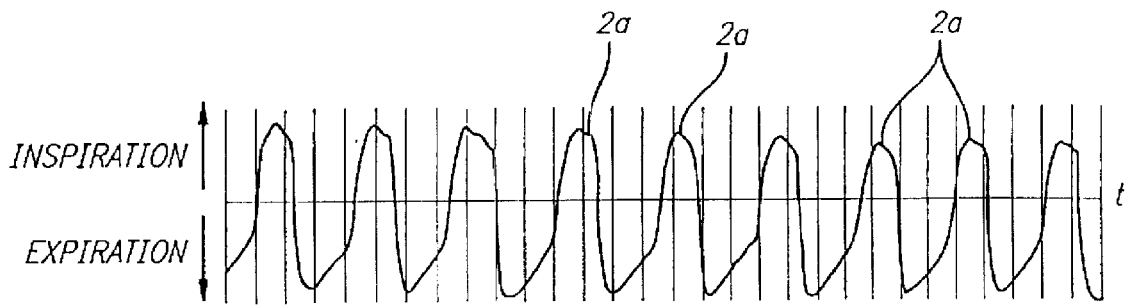
FIG. 2 shows a waveform of airflow from a sleeping patient in a 30 second epoch when subjected to a substantially constant PAP pressure of 8 cm $H_2O$.
Figure 3:
FIG. 3 shows a waveform of airflow from a sleeping patient in a 30 second epoch when subjected to a substantially constant PAP pressure of 6 cm $H_2O$.
Figure 4:
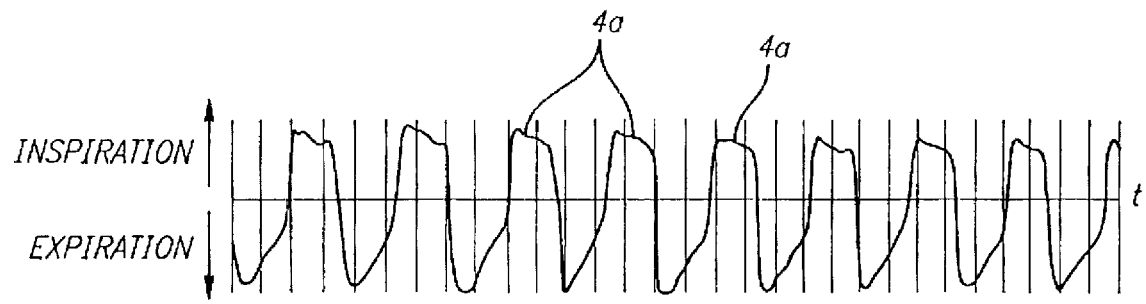
FIG. 4 shows a waveform of airflow from a sleeping patient in a 30 second epoch when subjected to a substantially constant PAP pressure of 4 cm $H_2O$.
Figure 5:
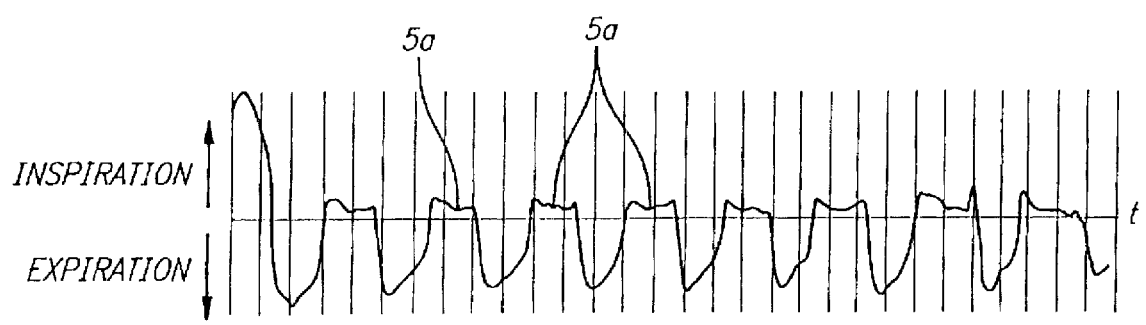
FIG. 5 shows a waveform of airflow from a sleeping patient in a 30 second epoch when subjected to a substantially constant PAP pressure of 2 cm $H_2O$.

When CPAP is decreased to 8 cm $H_2O$, as illustrated in FIG. 2, a partial flattening of the inspiratory flow waveform, at region 2a, begins to occur. This flattening becomes more definite when the CPAP is decreased to 6 cm $H_2O$, as seen in the region 3a of FIG. 3. The flattening becomes even more pronounced, as seen in the region 4a of FIG. 4, when the CPAP is reduced to 4 cm $H_2O$. These reductions in the CPAP from the pressure of apnea free respiration, result in, for example, snoring or other signs of patient airway obstruction. When the CPAP is further reduced to 2 cm $H_2O$, as illustrated in FIG. 5, inspiratory flow may decrease to a virtually zero level during inspiratory effort, as seen in the region 5a. Shortly after the recording of the waveform of FIG. 5, the patient in the example develops frank apnea and is awakened.

Figure 6:
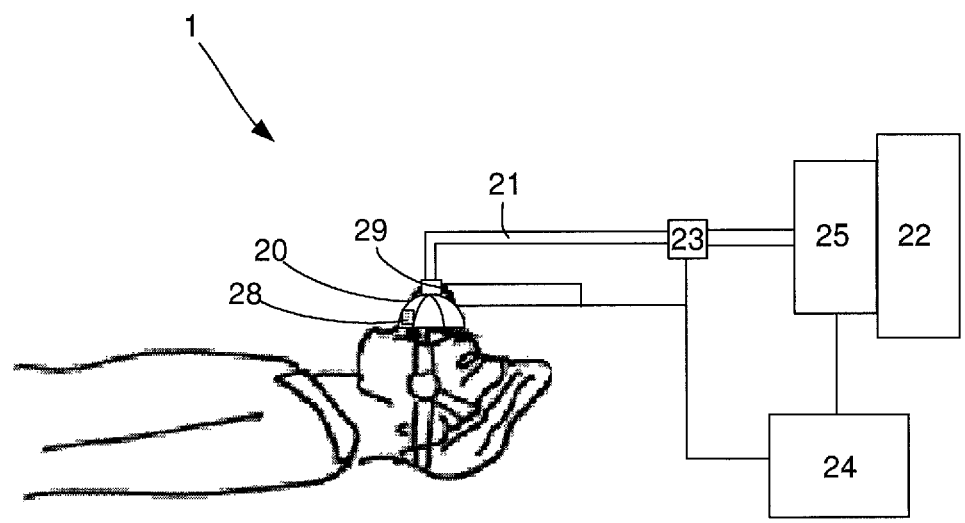
FIG. 6 shows an exemplary embodiment of a system according to the present invention.

FIG. 6 shows an exemplary embodiment of a system 1 according to the present invention. The system 1 may include a mask 20 which is connected via a tube 21 to receive airflow from a flow generator 22. A conventional flow sensor 23 is coupled to the tube 21 and detects an airflow pressure in the tube 21. A signal corresponding to the airflow pressure is provided to a processing arrangement 24 for processing. The processing arrangement 24 outputs a signal to a conventional flow control device 25 to control a pressure applied to the flow tube 21. Those skilled in the art will understand that, for certain types of flow generators which may by employed as the flow generator 22, the processing arrangement 24 may directly control the flow generator 22, instead of controlling flow therefrom by manipulating a separate flow control device 25.

The system 1 also includes a venting arrangement 28. The venting arrangement 28, for example, may include a valve mounted in an opening located, for example, on the mask 20 as shown in FIG. 6. Such an embodiment is described in greater detail later on with reference to FIG. 8. In the alternative, the opening may be located in an area of the tube 21 which is in close proximity to the mask 20. The valve may, for example, be a remotely operated non-re-breathing valve with a venting tube, such as a pneumatic or electromagnetic valve.

As would be understood by those skilled in the art, the venting arrangement 28 may be moved between an "open" position during a diagnostic mode and a "closed" position during a therapeutic mode under control of the processing arrangement 24. Specifically, when the venting arrangement 28 is in the open position, the venting tube of the venting arrangement 28 is partially or completely open to the atmosphere (e.g., via an opening) while remaining connected to the interior of the mask 20 at a distal end, thus allowing air to escape from the mask 20 (e.g., via the same opening). Thus, in one embodiment of the present invention, when the venting arrangement 28 is in the "open" position, no net pressure is supplied to the patient from the flow generator 22. As will be described in greater detail later on, the pressure from the flow generator 22 may range from 0-1 cm $H_2O$ in this position. When the venting arrangement is in the "closed" position, a valve of the venting arrangement 28 substantially prevents air leakage from the opening so that the mask 20 is substantially separated from the ambient environment. However, the venting arrangement 28 may be configured to permit a small leakage thereoutof so that gases exhaled by the patient may be diverted from the incoming air to prevent re-breathing thereof. This small leakage may be facilitated by the same opening open to the ambient environment during the diagnostic mode or, in another embodiment, may be an additional opening formed on the venting arrangement at or near the mask 20.

In an alternative exemplary embodiment of the present invention, the system 1 may include a further sensor 29 situated at or near the mask 20. The sensor 29 is also connected to the processing arrangement 24 and provides data thereto regarding the patient's breathing and/or the air pressure in the mask 20.

When the diagnostic mode is selected (e.g., by the patient, a physician/operator), the system 1 opens the valve of the venting arrangement 28 to run in a diagnostic mode, the diagnostic mode being indicative of, for example, a low pressure being supplied by the flow generator 22. The diagnostic test determines whether the patient has the breathing disorder during a period when no PAP is applied and patient breathing is being monitored. Once the valve is the open position and open to the ambient atmosphere, the flow generator 22 is activated to provide a predetermined flow rate to the mask 20 of the patient. The sensor 23 and the further sensor 29 are collecting data which is provided to the processing arrangement 24. Based on the data provided over a predetermined time period, the processing arrangement 24 can determine the breathing disorder and whether PAP is necessary for treatment of the breathing disorder.

Once the system 1 determines that PAP is necessary, the diagnostic mode is completed, and the system 1 switches to the therapeutic mode. The system 1 sets the PAP to be supplied to the patient to the value determined by analysis of the prior periods or a prior diagnostic mode if, for example, the current diagnostic mode malfunctions, data becomes corrupt, etc. Then, the valve of the venting arrangement 28 is switched to the closed position so that there is substantially no unintended leaking from the mask 20. The flow generator is activated and the determined PAP is provided to the patient. The processing arrangement 24, based on the data provided by the sensor 23 and the further sensor 29, may adjust the airflow rate of the flow generator to allow the PAP pressure to be at the desired level. Alternatively, the PAP pressure may be further modified based on the monitoring of airflow during a prior therapeutic period.

Figure 7:
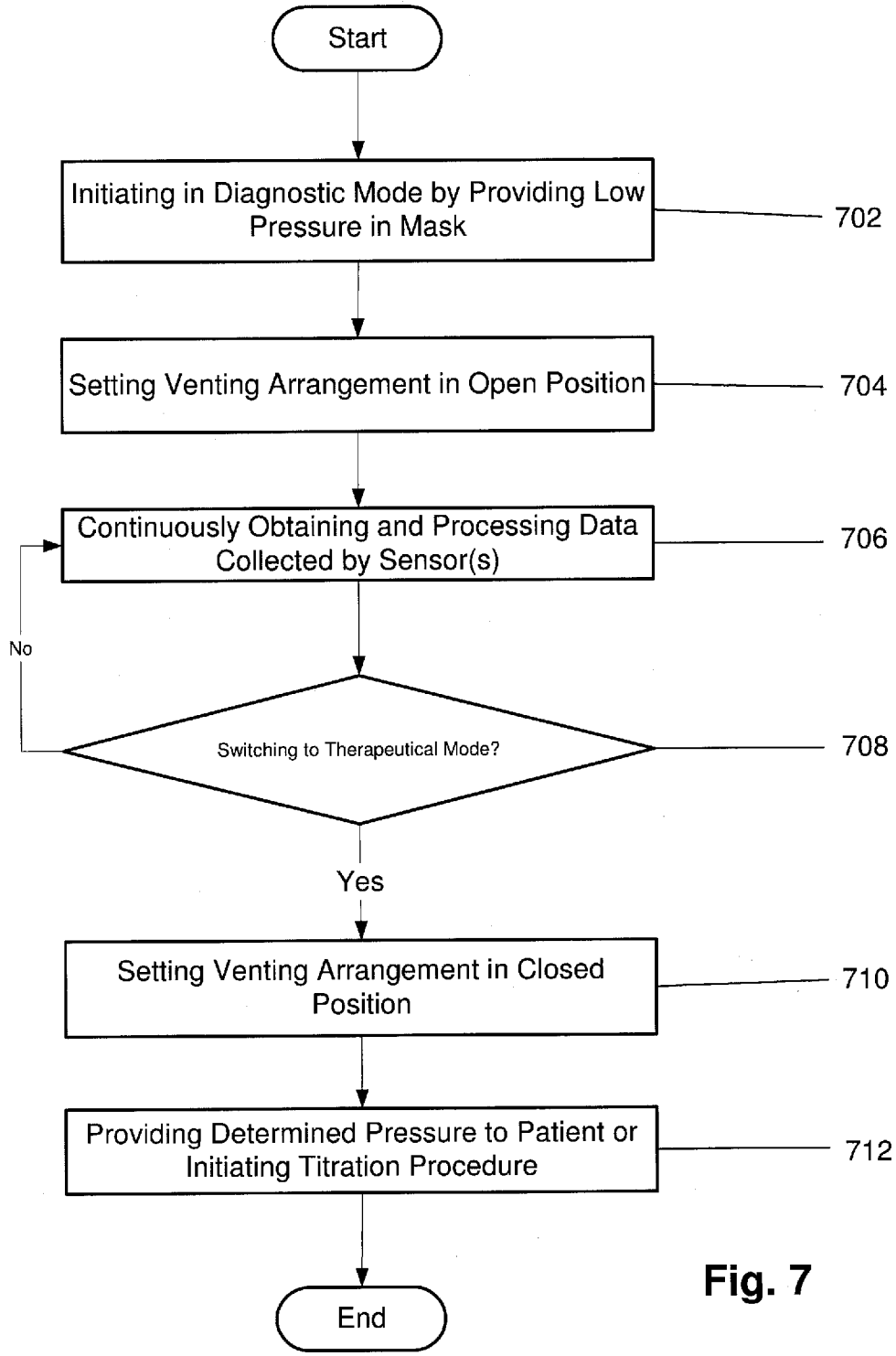
FIG. 7 shows an exemplary embodiment of a method according to the present invention.

FIG. 7 shows a method according to the present invention of operation of the system 1 described above in regard to FIG. 6. On an initial use of the system 1 by the patient, or when for any reason re-calibration or a new diagnosis is required, the system 1 is initiated in the diagnostic mode. Those skilled in the art will understand that the diagnostic mode may be initiated upon receipt of an explicit instruction from the patient or the physician/operator (e.g., by setting an actuator to the diagnostic mode) and/or by a command generated by the processing arrangement 24 when a predetermined condition is satisfied. For example, the processing arrangement 24 may automatically initiate the diagnostic mode when data indicates that the supplied PAP is incorrect or may simply run the diagnostic mode whenever a predetermined time has elapsed since the prior diagnostic mode.

Thus, when the diagnostics mode is begun, the valve of the venting arrangement 28 is moved to the open position. In step 702, the flow generator 22 supplies a low air pressure via the tube 21 to the mask 20. The provided airflow rate remains relatively constant (e.g., 10-20 l/min) at the mask 20. This flow rate may be achieved by setting a supply pressure from the flow generator 22 at, for example, approximately 1-3 cm $H_2O$.

As stated above, the flow generator 22 may be controlled via the flow control device 25 which receives signals from the processing arrangement 24. The processing arrangement 24 collects the data from the sensor 23 and the further sensor 29, monitors the data and adjusts the signals sent to the flow control device 25, if necessary, to achieve desired flow rate.

In step 704, the venting arrangement 28 is set, by the processing arrangement 24, in the open position. Thus, the generated air pressure is substantially dissipated by this leak. In one exemplary embodiment, the air pressure supplied to the mask 20 from the flow generator 22 may be reduced or eliminated so that a pressure in the mask 20 is maintained less than 0.5-1 em $H_2O$. Thus, the created leak should be made large enough so that pressure does not build up in the mask 20 even during patient exhalation to prevent problems associated with re-breathing $CO_2$.

In step 706, the processing arrangement 24 continuously monitors and analyzes, in real time, for example, the data collected by the flow sensor 23 and/or the further sensor 29. The data may include information about breathing patterns of the patient with or without the application of PAP, the pressure in particular portions of the system 1, etc. The processing arrangement 24 analyzes the data to detect any occurrence of a flow limitation event and/or the breathing disorders (e.g., (a) apnea in the form of short pauses which may be less than one minute, (b) hypopnea in the form of intermittent reductions in flow, etc.). As understood by those skilled in the art, flow limitation events and/or periods of flow limitation are detected as changes in the contour of the flow signal with transient flatting which indicates an elevated resistance in the patient's upper airways. Based on the data collected over several periods of patient therapy, the processing arrangement 24 may also determine the PAP necessary for treatment of the patient.

Subsequently, the processing arrangement 24 ends the diagnostic mode and switches into a therapeutic mode (step 708). For example, the switch to the therapeutic mode may occur upon predetermined criteria, such as, when the processing arrangement 24 detects a predetermined number of the flow limitation events within a predetermined period of time (e.g., an average of 30 events per hour within any two hour period). The switch may also occur after the processing arrangement 24 determines the PAP for the patient.

In the therapeutic mode, the processing arrangement 24 switches the valve of the venting arrangement 28 into the "closed" position (step 710). The flow generator 22 is then activated to deliver a predetermined PAP (e.g., PAP determined in the diagnostic mode) to the patient or, in the alternative, to perform a titration procedure. The titration procedure may consist of multiple prolonged sessions ranging from a few minutes to a few days of constant PAP, the patient being subsequently analyzed to test the effectiveness of the titration procedure in a manner substantially identical to the diagnostic mode of analysis as described above in step 702. Alternatively, the titration procedure may consist of a period during which auto-PAP (e.g., self-titrating PAP) is allowed to function, wherein a new predetermined PAP may be set for ongoing therapy. (step 712). Thus, in this mode the mask pressure builds to a predetermined level (e.g., 5-20 cm $H_2O$) to provide PAP to the patient sufficient to prevent collapse of the upper airways.

Thus, the system 1 can function in both the diagnostic mode and a therapeutic mode in a single unmonitored session. Those skilled in the art will appreciate that, once in the therapeutic mode, the system 1 may provide the PAP under any of a wide range of controls which are constant or vary with time, and that this system 1 is compatible with most known PAP systems.

In a further exemplary embodiment of the present invention, the system 1 may determine the PAP over the course of several sleeping cycles to arrive at a more accurate image of the patient's breathing patterns. For example, some patients may have "good" or "bad" nights which may not be representative of an "average" night for the patient. Thus, the diagnostic mode may continue for several nights, and, as such, may provide a more accurate pressure supplied to a particular patient. Additionally, application of the PAP during the therapeutic mode may not be limited temporally. That is, the system 1 may remain in the therapeutic mode for any amount of time (e.g., hours, days, sleep cycles, etc.).

In yet a further exemplary embodiment of the present invention, the system 1 may complete the diagnostic mode and the therapeutic mode over a single sleep cycle (e.g., from sleep to wake). For example, the system 1 may run in the diagnostic mode for a first predetermined time of the sleep cycle (e.g., 2 hours), and, at the expiration of that time, the PAP determined in the diagnostic mode is applied in the therapeutic mode for a second predetermined time of the sleep cycle (e.g., until wake).

In yet a further exemplary embodiment of the present invention, the PAP may be determined in the diagnostic mode using an obstruction index ("OI"). The OI may combine several indices of elevated resistance, such as snoring and flow limitation ("FL"), into one value. For example, in one exemplary embodiment, the OI includes a sum of an apnea/ hypopnea index ("AHI") and an amount of time sustained FL. The AHI may be the number of discrete FL events (10-120 seconds) per hour, and the amount of time in sustained FL may be greater than two minutes. The OI may correspond to severity of an excessive daytime sleepiness ("EDS") measured subjectively. The OI may further correspond to daytime function measured using a pyschomotor vigilance task ("PVT"). Thus, the OI may detect changes in a pattern of sleep-disordered breathing ("SDB") which are produced by increased levels of collapsibility and resistance of the upper airway.

Figure 8:
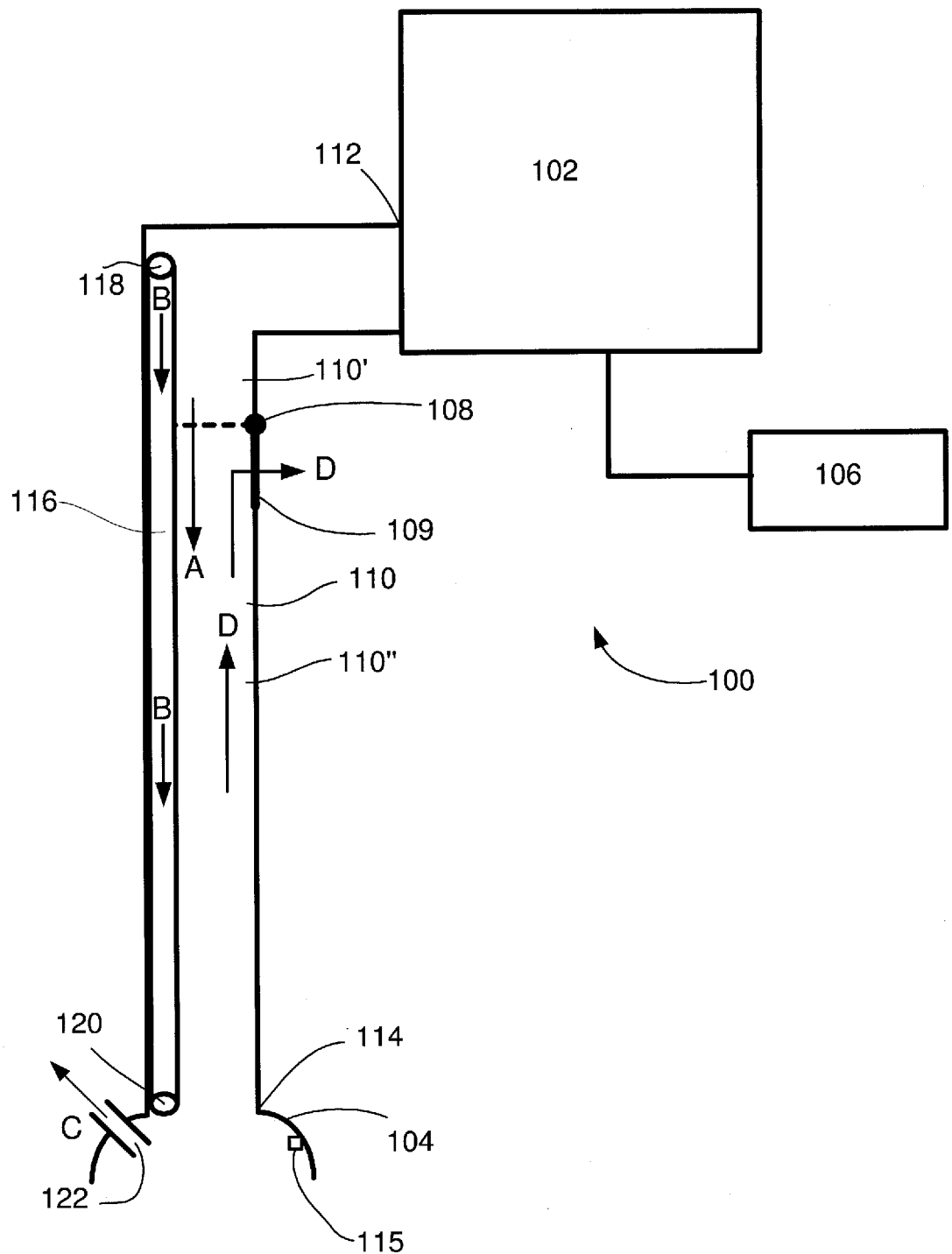
FIG. 8 shows a first exemplary embodiment of a CPAP valve device according to the present invention.

FIG. 8 shows a system 100 according to a first exemplary embodiment of the present invention, the system 100 being configured with a valve 108 movable to first and second configurations when the system 100 is in the therapeutic and diagnostic modes, respectively. The system 100 comprises a CPAP blower 102 configured to provide pressurized air to a patient via a first conduit 110. The CPAP blower 102 is connected to a computer 106 configured to control the flow of pressurized air through the system 100, as those skilled in the art will understand. The first conduit 110 extends from a proximal end 112 connected to the CPAP blower 102 to a distal end 114 connected to a respiratory mask 104 covering a respiratory orifice (e.g., nasal cavity or oral cavity) of a patient (not shown). A leak port 122 is located on the respiratory mask 104 to provide a continuous exit of exhaled gas from the system 100 when a pressure therein is greater than approximately 3-5 cm $H_2O$. It is noted that although the leak port 122 is shown on the mask 104 of the present invention, the leak port 122 may also be positioned elsewhere on the system 100 at a location that is substantially adjacent to the respiratory orifice of the patient. The first conduit 110 is formed of a substantially flexible and durable material known in the art and is dimensioned to permit a predetermined volume of air therethrough at a predetermined pressure, as those skilled in the art will understand. The system 100 also comprises a second conduit 116 open to the mask 104. The second conduit 116 extends from a proximal end 118 open to a proximal portion of the first conduit and the CPAP blower 102 to a distal end open to the mask 104. As will be described in greater detail below, the device 100 of the present invention is configured to bypass a need for a suctioning device to draw exhaled gas out of the system. It is noted however, that an optional suctioning device may be incorporated in the system 100 without deviating from the spirit and scope of the present invention. It is further noted that although the second conduit 116 is shown to extend through the first conduit 110, the second conduit 116 may alternatively assume any position relative thereto as long as the distal end 120 opens into the mask 104 and provides a means for exhaled gas from the respiratory orifice to be removed independently of a pressure in the mask 104. For example, in a first alternate embodiment, the second conduit 116 may be located externally of the first conduit 110 as long as the proximal and distal ends 118, 120 are fluidly connected to the CPAP blower 102 and mask 104, respectively.

The valve 108 is configured to selectively seal an opening 109 located adjacent thereto. The valve 108 is a two-way valve located substantially adjacent the proximal end 112 of the first conduit 110. The valve 108 is connected to the computer 106 via one of a wired and a wireless connection. Thus, the computer 106 can automatically move the valve 108 from a first position to a second position when a predetermined condition is met, as will be described in greater detail hereinafter. In a first position, the valve 108 is configured to fluidly seal the opening 109 while leaving the first conduit 110 substantially unobstructed so that air can flow therethrough. In a second position, the valve 108 is moved so that the first conduit 110 is substantially sealed to airflow. Specifically, movement of the valve 108 to the second position fluidly seals a proximal portion 110' of the first conduit 110 located proximally of the valve 108 with respect to a distal portion 110" located distally thereof. In the second position, the opening 109 is fluidly connected to the distal portion 110" so that the distal portions 110" is open to the atmosphere, as will be described in greater detail hereinafter.

In accordance with an exemplary method of the system 100, the proximal end 112 of the first conduit 110 is connected to the CPAP blower 102 and the distal end 114 to the respiratory mask 104. When the valve 108 is in the first position (i.e., when a positive air pressure exceeding a predetermined limit is being supplied), the first and second conduits 110, 116 remain unobstructed and positive air is guided through each of the first and second conduits 110, 116 in the directions A and B, respectively. Exhaled gas from the patient is then guided out of the system 100 via the leak port 122 located on the mask 104. In an exemplary embodiment, the valve 108 remains in the first operative position as long as the positive air supply has a pressure greater than 5 cm. $H_2O$, wherein the pressure is selected based on the breathing parameters of the patient, as those skilled in the art will understand. It is noted that the system 100 may further comprise a sensor 115 located in any of the components thereof to monitor pressure and/or flow, as those skilled in the art will understand.

When the pressure of the positive air supply falls below 5 cm. $H_2O$, the valve 108 moves to the second position. Movement of the valve 108 to the second operative position ensures that exhaled $CO_2$ is properly ventilated from the system 100. Specifically, in the second position, the first conduit 110 is sealed to airflow such that positive airflow is only permitted in the direction B through the second conduit 116. The second conduit 116 is sized and shaped so that air flow therethrough has a pressure of approximately 25 l/min. Exhaled $CO_2$ from the respiratory orifice of the patient then travels in the direction C to exit the leak port 122. Furthermore, the exemplary embodiment of the present invention also guides the exhaled $CO_2$ in the direction D through the first conduit 110 and out of the opening 109. Thus, whereas present CPAP devices would prevent a leakage of $CO_2$ at low pressure, the exemplary embodiment of FIG. 1 facilitates venting of $CO_2$ from the system 100 when the air pressure in the system 100 falls below a predetermined parameter. The valve 108 remains in the second position until a CPAP air pressure once again exceeds 5 cm. $H_2O$ (e.g., when the patient returns to a sleeping state, etc.).

The sensor 115 may be provided within one of the mask 104 or in the distal portion 110" of the first conduit 110 located distally of the valve 108 and be configured to measure the patient's breathing patterns and make a determination of a pressure within the system 100. As those skilled in the art will understand, the sensor 115 may be positioned anywhere within the system 100 so that the sensor 115 is provided with data corresponding to a patient's breathing patterns regardless of a position of the valve 108. The sensor 115 may be connected to a database containing data corresponding to breathing patterns indicative of each of the diagnostic and therapeutic modes. The database may be compiled with data from the patient or from a plurality of test subjects, as those skilled in the art will understand. The valve 108 may then be configured to remain in the first position when the sensor 115 is indicative of the therapeutic mode. As described in greater detail earlier, in the first position, the opening 109 may be sealed so that a positive air flows travels in the directions A, B and the leak port 122 permits exhaled gas to leave the system 100. When the sensor 115 indicates that a pressure within the system 100 has lowered to a predetermined level or range, the valve 108 may move to the second position so that the opening 109 is open to the environment. Movement of the valve 108 from the first position to the second position then prevents airflow from the CPAP blower to travel through the first conduit 110 to the patient.

It is noted that the embodiment of FIG. 8 is exemplary only and that the system and method according to the present invention may alternately be performed by a plurality of other designs without deviating from the scope of the present invention. Furthermore, it will be apparent to those skilled in the art that various modifications and variations can be made in the structure and the methodology of the present invention, without departing from the spirit or scope of the invention. For example, the flow sensor 23 and the further sensor 29 may be employed interchangeably without deviating from the spirit and scope of the present invention. Thus, it is intended that the present invention cover the modifications and variations of this invention provided they come within the scope of the appended claims and their equivalents.

What is claimed is:

1. A system for diagnosis and treatment of breathing disorders in a patient, comprising:
    a flow generator supplying an airflow to an airway of a patient via an air flow path;
    a venting arrangement moveable between (i) a closed position in which the flow path is substantially sealed from an ambient atmosphere between the flow generator and the patient's airway, and (ii) an open position in which the flow path is open to the ambient atmosphere;
    a sensor detecting data corresponding to flow through the patient's airway; and
    a processing arrangement controlling operation of the venting arrangement and the flow generator,
    wherein, in a diagnostic mode, the processing arrangement maintains the venting arrangement in the open position and monitors airflow through the patient's airway using the data provided by the sensor, and
    wherein, in a therapeutic mode, the processing arrangement maintains the venting arrangement in the closed position and controls the flow generator to supply to the patient's airway via the flow path a therapeutic pressure calculated based on the data compiled in the diagnostic mode.

2. The system according to claim 1, further comprising a tube and a mask coupled to the flow generator.

3. The system according to claim 2, wherein the sensor includes a pressure sensor sensing pressure in the mask.

4. The system according to claim 1, wherein the venting arrangement allows a leak from the flow path sufficient to prevent $CO_2$ buildup.

5. The system according to claim 1, wherein the diagnostic mode is initiated by one of the patient and an operator.

6. The system according to claim 1, wherein the diagnostic mode is automatically initiated by the processing arrangement.

7. The system according to claim 1, wherein, upon predetermined criteria, the diagnostic mode switches to the therapeutic mode.

8. The system according to claim 7, wherein the predetermined criteria is one of (i) a predetermined time, (ii) a value corresponding to flow limitation events, (iii) when the therapeutic pressure is determined in the diagnostic mode, (iv) patient-determined and (v) operator-determined.

9. The system according to claim 8, wherein the predetermined time is a predetermined portion of at least one sleep cycle of the patient.

10. The system according to claim 8, wherein the predetermined time is at least one sleep cycle of the patient.

11. The system according to claim 8, wherein the value corresponding to flow limitation events is one of a predetermined number of flow limitation events and an obstruction index.

12. The system according to claim 1, wherein, in the therapeutic mode, the processing arrangement controls the flow generator to supply the therapeutic pressure based on a plurality of data measurements compiled from multiple diagnostic sessions.

13. A method for diagnosis and treatment of breathing disorders in a patient, comprising the steps of:
    initiating a diagnostic mode in which a processing arrangement controls a venting arrangement to an open position in which a flow path between the flow generator and the patient's airway is open to an ambient atmosphere;
    detecting, with a sensor, data corresponding to flow through the patient's airway;
    monitoring airflow through the patient's airway using data provided by the sensor;
    upon a predetermined criteria, initiating a therapeutic mode in which the processing arrangement switches the venting arrangement into the closed position and controls the flow generator to supply to the patient's airway via the flow path a therapeutic pressure calculated based on the data compiled in the diagnostic mode.

14. The method according to claim 13, further comprising a tube and a mask coupled to the flow generator.

15. The method according to claim 13, wherein the sensor includes a pressure sensor sensing pressure in the mask.

16. The method according to claim 13, wherein the venting arrangement allows a leak from the flow path sufficient to prevent $CO_2$ buildup.

17. The method according to claim 13, wherein the diagnostic mode is initiated by one of the patient and an operator.

18. The method according to claim 13, wherein the predetermined criteria is one of (i) a predetermined time, (ii) a value corresponding to flow limitation events, (iii) when the therapeutic pressure is determined in the diagnostic mode, (iv) patient-determined and (v) operator-determined.

19. The method according to claim 18, wherein the predetermined time is a predetermined portion of at least one sleep cycle of the patient.

20. The method according to claim 18, wherein the predetermined time is at least one sleep cycle of the patient.

21. The method according to claim 18, wherein the value corresponding to flow limitation events is one of a predetermined number of flow limitation events and an obstruction index.

22. The system according to claim 1, wherein when the venting arrangement is in the closed position, the flow path is sealed from the ambient atmosphere between the flow generator and the patient's airway.

\* \* \* \* \*